United States Patent [19]

Geiger et al.

[11] Patent Number: 4,595,675
[45] Date of Patent: Jun. 17, 1986

[54] BICYCLIC α-IMINOCARBOXYLIC ACID COMPOUNDS HAVING HYPOTENSIVE ACTIVITY

[75] Inventors: Rolf Geiger, Frankfurt am Main; Volker Teetz, Hofheim am Taunus; Bernward Schölkens, Kelkheim; Hans Wissmann, Bad Soden am Taunus, all of Fed. Rep. of Germany

[73] Assignee: Hoechst Aktiengesellschaft, Frankfurt am Main, Fed. Rep. of Germany

[21] Appl. No.: 688,325

[22] Filed: Jan. 2, 1985

Related U.S. Application Data

[63] Continuation-in-part of Ser. No. 520,227, Aug. 5, 1983, abandoned, which is a continuation of Ser. No. 188,228, Sep. 17, 1980, abandoned, and Ser. No. 534,392, Sep. 22, 1983, abandoned, which is a continuation of Ser. No. 324,141, Nov. 23, 1981, abandoned.

[30] Foreign Application Priority Data

Sep. 19, 1979 [DE] Fed. Rep. of Germany ....... 2937779
Nov. 21, 1979 [DE] Fed. Rep. of Germany ....... 2946909
Nov. 25, 1980 [DE] Fed. Rep. of Germany ....... 3044236

[51] Int. Cl.⁴ .................. C07D 5/06; A61K 37/02
[52] U.S. Cl. .................. 514/10; 530/800; 546/140; 546/147; 546/164; 546/168; 546/148; 548/455; 548/465; 548/469; 514/929
[58] Field of Search .............. 546/164, 147, 140, 168; 514/307, 308, 10; 548/455, 465; 260/112.5

[56] References Cited

U.S. PATENT DOCUMENTS

| 4,116,962 | 9/1978 | Ondetti et al. | 260/112.5 |
| 4,179,434 | 12/1979 | Ondetti et al. | 514/10 |
| 4,256,751 | 3/1981 | Hayoshi et al. | 546/147 |
| 4,291,163 | 9/1981 | Wright et al. | 546/164 |
| 4,303,583 | 12/1981 | Kim et al. | 260/239.3 T |
| 4,344,949 | 8/1982 | Hoefle et al. | 546/141 |
| 4,350,704 | 9/1982 | Hoefle et al. | 546/147 |
| 4,374,829 | 2/1983 | Harris et al. | 260/112.5 |
| 4,404,206 | 9/1983 | Vincent et al. | 546/147 |
| 4,470,973 | 9/1984 | Natarajan et al. | 260/112.5 |
| 4,472,381 | 9/1984 | Sakakibaar et al. | 260/112.5 |
| 4,472,383 | 9/1984 | Oka et al. | 260/112.5 |
| 4,500,713 | 2/1985 | Suh et al. | 546/165 |
| 4,503,043 | 3/1985 | Blankley | 514/10 |
| 4,532,342 | 7/1985 | Hoefle et al. | 560/38 |

FOREIGN PATENT DOCUMENTS

| 5472780 | 8/1980 | Australia | 546/147 |
| 6141780 | 2/1981 | Australia | 548/492 |
| 6512380 | 6/1981 | Australia | 546/147 |
| 0012845 | 7/1980 | European Pat. Off. | 546/147 |
| 0018104 | 10/1980 | European Pat. Off. | 546/147 |
| 0050800 | 6/1982 | European Pat. Off. | 546/147 |
| 2443533 | 9/1980 | France | 546/147 |
| 2042535 | 9/1980 | United Kingdom | 546/147 |
| 2048863 | 12/1980 | United Kingdom | 546/147 |

Primary Examiner—Glennon H. Hollrah
Assistant Examiner—D. L. Dinner
Attorney, Agent, or Firm—Curtis, Morris & Safford

[57] ABSTRACT

What are disclosed are indole, quinoline and isoquinoline compounds of the formula

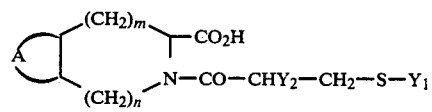

in which n denotes 0 or 1, m denotes 1 or 2, but $(n+m) \leq 2$, A together with the bridgehead carbon atoms denotes a benzene or a cyclohexane ring, $Y_1$ denotes hydrogen, lower alkanoyl or lower cycloalkanoyl, benzoyl nicotinoyl or a radical of the formula II, and $Y_2$ denotes methyl, amino, lower alkanoylamino, lower cycloalkanoylamino, benzoylamino or nicotinoylamino, and salts thereof, useful as hypotensive agents, and methods for making the same.

15 Claims, No Drawings

BICYCLIC α-IMINOCARBOXYLIC ACID COMPOUNDS HAVING HYPOTENSIVE ACTIVITY

This application is a continuation-in-part application of U.S. application Ser. No. 520,227 filed Aug. 5, 1983, which is a continuation application of U.S. application Ser. No. 188,228 filed Sept. 17, 1980, and of U.S. application 534,392 filed Sept. 22, 1983, which is a continuation application of U.S. application Ser. No. 324,141 filed Nov. 23, 1981, all now abandoned.

The invention relates to compounds of the formula I

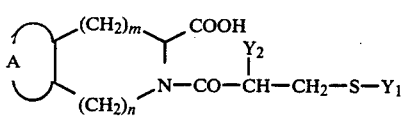

in which n denotes 0 or 1, m denotes 1 or 2, but (n+m)≦2,

A together with the bridgehead carbon atoms denotes a benzene or a cyclohexane ring, $Y_1$ denotes hydrogen, lower alkanoyl or lower cycloalkanoyl, benzoyl or a radical of the formula II, m and n each preferably having the same meaning in both halves of the molecule

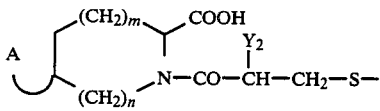

or, if

A is part of a benzene ring then $Y_1$ is as defined above or denotes nicotinoyl, and $Y_2$ denotes methyl, amino, lower alkanoylamino, lower cycloalkanoylamino or benzoylamino, or, if A is part of a benzene ring then $Y_2$ is as defined above or denotes nicotinoylamino, or the salts thereof.

Lower alkanoyl as defined above denotes, in particular, alkanoyl having 1 to 6 C atoms or lower cycloalkanoyl, particularly cycloalkanoyl having 5 to 8 C atoms.

Similar to many other derivatives of indoline and 1,2,3,4-tetrahydroquinoline, the compounds according to the invention have valuable pharmacological properties.

The invention also relates to a process for the preparation of these compounds. This process comprises reacting a lower alkyl ester of an iminoacid of the formula III

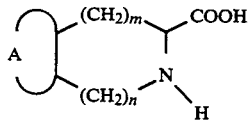

or a salt of such iminoacid with a strong, non-volatile base, with an activated derivative of a carboxylic acid of the formula IV

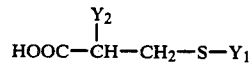

in which $Y_1$ is not H, splitting off the base or the ester group, respectively, from the resulting product, if appropriate splitting off an acid radical in the position $Y_1$ or replacing it by another acid radical, and, if the compound has a free SH group, oxidizing the product, if desired, to give the disulfide compound.

The synthesis of the compounds of the invention is simple. The indoline-2-carboxylic acid suitable as starting compound is known from Aust. J. Chem. 20, page 1935 (1967) and 1,2,3,4-tetrahydroquinoline-2-carboxylic acid is known from Chem. Ber. 61, page 2377 (1928).

1,2,3,4-Tetrahydroisoquinoline-3-carboxylic acid used as starting material is easily accessible by reaction of phenyl aniline with formaldehyde as described in J. Amer. Chem. Soc. 70, page 182 (1948).

The starting compounds wherein A is part of a cyclohexane ring can be synthesized by subjecting the known compounds indole-2-carboxylic acid, quinoline-2-carboxylic acid or 1,2,3,4-tetrahydro-isoquinoline-3-carboxylic acid to catalytic hydrogenation. Preferred catalysts are platinum and rhodium, and these are used at temperatures of up to about 100° C. and under pressures of up to about 150 bar.

Carboxylic acids of the formula IV, especially

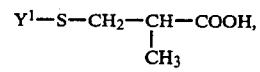

are described, inter alia in DE-OS No. 2,752,720 as well as its English language equivalent U.S. Pat. No. 4,116,962 or they can be prepared in analogous manner.

The compound of the formula IV in which $Y_2$ denotes nicotinoylamino is prepared from thionicotinic acid and methacrylic acid in a manner similar to that described in DE-OS No. 2,845,499.

Suitable derivatives of cysteine are known from the literature.

The acid amides are prepared according to conventional methods, preferably those of peptide chemistry, for example as described in detail in Houben-Weyl, Methoden der Organischen Chemie ("Methods of Organic Chemistry"), Volume 15.

Examples of suitable activated derivatives of a carboxylic acid of the formula IV are the acid chlorides, active esters, mixed anhydrides with any desired other carboxylic acids or carbonic acid half-esters. They can be reacted directly with iminoacids of the formula III or salts thereof as discussed previously. Bases are understood as meaning primarily alkali metal hydroxides or alkaline earth metal hydroxides. In addition, examples of suitable strong, non-volatile organic bases in the sense of the invention are tetraalkylammonium or tetraaralkylammonium hydroxides or tetra-alkylated guanidines, such as tetramethylguanidine.

Activated esters can be prepared, for example, from the corresponding acid and N-hydroxysuccinimide, 2,4,5-trichlorophenol or 1-hydroxybenzotriazole in a known manner by means of dicyclohexylcarbodiimide, and, after removing the dicyclohexylurea formed in their preparation, are used at once in solution. Preferred solvents are dimethylformamide, dimethylacetamide, N-methylpyrrolidone, phosphoric acid tris-dimethylamide or methylene chloride. The same solvents are used to dissolve the salts, according to the invention, of the iminoacids of the formula III, which have previously been obtained from the components in equimolar quantities, for example in an alcoholic or aqueous-alcoholic solution, and have been freed from the solvent, for example by distilling off the latter in vacuo.

Compounds in which $Y_1$ denotes hydrogen can be obtained by treating the corresponding S-acyl derivatives with ammonia or alkali metal or alkaline earth metal hydroxides. The latter substances may simultaneously serve to saponify methyl or ethyl ester groups possibly being present.

The reaction can be carried out at room temperature and is complete after about 30 minutes when using the acid chlorides or after 14 hours at the most when using active esters. The solvent is then removed, for example by distillation in vacuo, and the crude product is purified, for example by liquid chromatography over silica gel, in which respect solvent systems containing chloroform, methanol and acetic acid have proved suitable.

However, it is also possible, as in the process which is preferred in peptide chemistry, the subject the carboxylic acids IV to a condensation reaction with alkyl esters of the iminoacids of the formula III and then to split or saponify the esters, the S-acyl linkage being split by alkali at the same time. The preferred condensation agent is dicyclohexylcarbodiimide, if appropriate with the addition of N-hydroxysuccinimide or 1-hydroxybenzotriazole. The preferred solvents are those mentioned above.

Compounds of the formula V

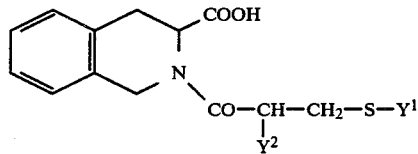
(V)

in which $Y_1$ denotes lower alkanoyl or lower cycloalkanoyl, benzoyl or nicotinoyl and $Y_2$ is methyl, lower alkanoylamino, lower cycloalkanoylamino, benzoylamino or nicotinoylamino can be obtained, for example, by reacting an ester of the formula VI

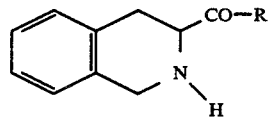
(VI)

in which R denotes the radical of an alcohol capable of being split off under acid conditions, for example the tert. butoxy radical, with a carboxylic acid of the formula IV. After acid splitting of the ester grouping —CO—R by reacting with ammonia, a primary or secondary amine or an alkali metal hydroxide and treatment of the salt with acid or a strongly acid ion exchanger, the radical $Y_1$ in the compounds thus obtained can then be replaced by hydrogen.

It is also possible to condense other alkyl esters, preferably the methyl or ethyl esters of 1,2,3,4-tetrahydroisoquinoline-3-carboxylic acid with a carboxylic acid of the formula IV and to treat the reaction product with an alkali metal hydroxide or alkaline earth metal hydroxide in order to split off the methyl or ethyl ester and the S-acyl group.

Another way of prepare compounds of the formula V in which $Y_1$ is hydrogen and $Y_2$ is amino is the condensation of a compound of the formula VI with N,S-ditert.butyloxycarbonyl cysteine with splitting off of the protective groups by a treatment with a strong acid, preferably in the presence of a cation acceptor carrying SH groups such as thiophenol, ethylmercaptan or dithioglycol.

Alternatively, a tetraalkylguanidinium, trialkylbenzyl, or tetraalkyl ammonium salt of 1,2,3,4-tetrahydroisoquinoline-3-carboxylic acid can be reacted with an activated derivative of a carboxylic acid IV and the salt obtained can be decomposed with an acid or a strongly acid ion exchanger. If desired, the products obtained can be further modified by splitting off the acyl group such as acetyl or benzoyl in position $Y_1$, for example by a treatment with ammonia, an alkali metal or alkaline earth metal hydroxide and, if appropriate, by a treatment with a mild oxidant such as air, iodine or potassium hexacyanoferrate(III) in order to introduce a radical of the formula II.

For example, it is also possible to react, with a carboxylic acid of the formula IV, an ester of the formula VII

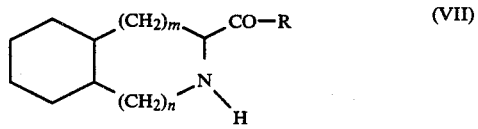
(VII)

in which R represents the radical of an alcohol which can be split off under acid conditions, for example tert.-butoxy. After splitting the ester under acid conditions, the radical $Y_1$ in the compounds thus obtained can be replaced by hydrogen by treating the product with ammonia, a primary or secondary amine or alkali metal hydroxide or alkaline earth metal hydroxide. The compound of the formula I in which $Y_1=H$ is liberated by further treatment with acid or with a strongly acid ion exchanger.

It is also possible to subject other alkyl esters, preferably methyl or ethyl esters, of decahydroisoquinoline-3-carboxylic acid to a condensation reaction with a carboxylic acid of the formula IV and to treat the reaction product with an alkali metal hydroxide or alkaline earth metal hydroxide in order to split off the ester group and the S-acyl group.

Compounds of the formula I in which $Y_1$ represents a radical of the formula II can also be prepared, for example, by reacting a compound of the formula III or salts or esters thereof, with a compound of the formula VIII

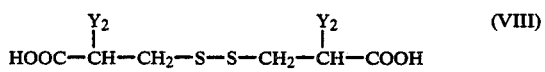
(VIII)

and, if desired, splitting off protective groups which may be present.

Compounds of the formula I in which $Y_1$ denotes nicotionyl can also be obtained by reacting a corresponding compound of the formula III with an activated derivative of nicotinic acid.

Depending on the character of the starting materials, particularly on the meaning of the substituents $Y_1$ and Y2, one or other of the processes described can, in individual cases, yield a desired individual compound only in poor yields or can be unsuitable for synthesizing it. In such cases, which occur relatively seldom, those skilled in the art experience no difficulties in synthesizing the desired product by another of the process routes described.

The compounds of the invention have 2 or more chiral centers. They are obtained in the form of resins and some of them can be converted to the solid state by a prolonged treatment with petroleum ether. They mostly melt with decomposition and they do not have a sharp melting point, which, besides, is strongly dependent on the time of heating. Their identity has been verified by elemental analysis, UV, IR and NMR spectroscopy.

By countercurrent distribution of their salts with optically active bases, stereochemically more uniform compounds can be obtained having a higher biological activity and a still unknown absolute configuration. In practice the more active compounds with prolonged activity can also be used in the form of the stereoisomeric mixture.

With peroral administration of 1 to 20 mg per kilogram and day, the indoline, 1,2,3,4-tetrahydroquinoline and 1,2,3,4-tetrahydroisoquinoline compounds according to the invention reduce blood pressure in the hypertonic rat and in dogs and they are effective in the same dosage range in human beings as well.

Octahydroindole, decahydroquinoline and decahydroisoquinoline compounds according to the invention are 2–4 times as effective as the corresponding benzenoid compounds with indoline-2-carboxylic acid, 1,2,3,4-tetrahydroquinoline-2-carboxylic acid or 1,2,3,4-tetrahydroisoquinoline-3-carboxylic acid and compounds in which the carboxylic acid of the formula IV is linked with proline in the manner of an acid amide.

When administered perorally at 0.5 to 20 mg per kg and per day to hypertensive rats and dogs, the perhydrocompounds according to the invention lower the blood pressure, and are also effective on humans within the same dosage range.

In animal experiments it was possible to increase the dose of all compounds tested without harmful effects.

The novel compounds can be used to combat hypertension of various geneses. They can be used either along or in combination with other blood pressure reducing, vasodilatory or diuretically active compounds.

Typical representatives of this class of active compounds are described, for example, in Erhardt-Ruschig, Arzneimittel ("Drugs") 2nd Edition, Weinheim 1972.

The invention is illustrated in greater detail by means of the following examples:

EXAMPLE 1

N-(2-Methyl-3-acetylmercaptopropionyl)-L-1,2,3,4-tetrahydroisoquinoline-3-carboxylic acid (A)
N-benzyloxycarbonyl-L-1,2,3,4-tetrahydroisoquinoline-3-carboxylic acid 35 g of L-1,2,3,4-tetrahydroisoquinoline-3-carboxylic acid, prepared from L-phenylalanine by condensation with formaldehyde according to J. Amer. Chem. Soc. 70, page 182 (1948), are suspended in 200 ml of 1N NaOH. While vigorously stirring, 30.2 ml of benzyloxycarbonyl chloride and 232 ml of 1N NaOH are simultaneously added slowly at 0° to 5° C. and stirring of the mixture is continued for 2 hours. The mixture is then extracted twice with ether, the aqueous solution is acidified with concentrated hydrochloric acid and shaken with ethyl acetate. The ethyl acetate phase is washed with water and dried over $Na_2SO_4$. After distillation of the solvent in vacuo, a resin is obtained which is dissolved in hot diisopropyl ether. The product crystallizes on cooling and after trituration. Yield 50.4 g, melting point 139° to 140° C.

$[\alpha]_D$: +23.9° (c=1 in methanol).

(B)
N-Benzyloxycarbonyl-L-1,2,3,4-tetrahydroisoquinoline-3-carboxylic acid tert. butyl ester 31.1 g of the compound obtained according to (A) are dissolved in 250 ml of methylene chloride. 38.5 g of tert. butanol and 1 g of 4-dimethylaminopyridine are added, and while stirring at 0° C., a solution of 22 g of dicyclohexyl carbodiimide in 60 ml of methylene chloride is added drop by drop. The mixture is stirred for 15 minutes at 0° C. and then for 5 hours at room temperature, filtered, and the filtrate is evaporated to dryness in vacuo. The residue is taken up in methylene chloride. The solution is successively shaken with sodium bicarbonate solution and potassium hydrogen sulfate/potassium sulfate solution, washed neutral with water and dried over $Na_2SO_4$. After concentration by evaporation, an oily residue is obtained. Yield 32.6 g.

(C) L-1,2,3,4-Tetrahydrosioquinoline-3-carboxylic acid tert. butyl ester toluene sulfonate 30.5 g of the compound prepared according to (B) are dissolved in 300 ml of methanol and catalytically hydrogenated on palladium black while maintaining a pH of 5 on an autotitrator by adding 1N toluene-sulfonic acid. When the reaction is terminated, the catalyst is filtered off and the solvent is distilled off. The resinous residue becomes solid after trituration with ether. Yield 31.4 g. The compound is chromatographically almost pure and differs from the starting compound by a lower $R_f$ value in a thin layer chromatogram.

(D)
N-(2-Methyl-3-acetylmercaptopropionyl)-L-1,2,3,4-tetrahydroisoquinoline-3-carboxylic acid tert. butyl ester 20.3 g of the tert. butyl ester tosylate prepared according to (C) are dissolved in 200 ml of methylene chloride, 8.3 g of 2-methyl-3-acetylmercaptopropionic acid, 6.4 ml of N-ethylmorpholine and, while cooling, 11 g of dicyclohexyl carbodiimide dissolved in 60 ml of methylene chloride are added. The mixture is stirred at room temperature over night, filtered, the solvent is distilled off in vacuo and the residue is taken up in ethyl acetate. The solution is successively washed with $NaHCO_3$ solution, $KHSO_4/K_2SO_4$ solution and water, dried over $Na_2SO_4$ and evaporated in vacuo. 16.3 g of oil are obtained.

(E)
N-(2-Methyl-3-acetylmercaptopropionyl)-L-1,2,3,4-tetrahydroisoquinoline-3-carboxylic acid 13 g of the compound obtained according to (D) are dissolved in 70 ml of trifluoroacetic acid which is distilled off in vacuo after 45 minutes. The residue is distributed between 180 ml of ethyl ether and 90 ml of saturated $NaHCO_3$ solution. The ether phase is rejected. The aqueous phase is acidified with concentrated hydrochloric acid and extracted three times with ethyl acetate. The combined ethyl acetate solutions are washed with water and dried over Na$_2$SO$_4$. The solvent is distilled off. The residue is taken up in ether and cyclohexylamine is added while stirring until moist pH paper indicates a value of 8. After cooling the suspension obtained, the cyclohexyl ammonium salt is filtered off and washed with ether. After drying the salt is recrystallized from isopropanol and acetonitrile. Melting point 159° to 161° C., $[\alpha]_D$: −11.5° (c=0.5 in methanol). Yield 4.8 g. In order to obtain the free acid, the salt is suspended between water and ethyl acetate/ether. After addition of KHSO$_4$ solution to pH 2, all is dissolved. The phases are separated. The aqueous solution is washed with a small amount of ethyl acetate and the combined organic phases are washed with a small amount of water, dried over Na$_2$SO$_4$ and the solvent distilled off in vacuo. The resinous residue becomes solid on rubbing with ether. Yield 3.0 g. Elemental analysis correct.

EXAMPLE 2

N-(2-Methyl-3-mercaptopropionyl)-L-1,2,3,4-tetrahydroisoquinoline-3-carboxylic acid 1.3 g of the compound prepared according to Example 1(E) in 8 ml of 5N ammonia are kept for 2 hours under nitrogen. Next, the solution is evaporated to dryness in vacuo and the solid residue is dissolved in 10 ml of 50% aqueous methanol. The solution is filtered over a small column of the strongly acid ion exchanger "Lewatit S 100" and the eluate is evaporated to dryness in vacuo. The resinous residue is digested in petroleum ether, whereupon it becomes solid. After drying in vacuo, the title compound is obtained in a yield of 0.85 g. The elemental analysis is correct.

EXAMPLE 3

N-D-Cysteinyl-L-1,2,3,4-tetrahydroisoquinolin-3-carboxylic acid (A)
N-S-Di-Boc-D-cysteinyl-L-1,2,3,4-tetrahydroisoquinoline-3-carboxylic acid tert. butyl ester 4.36 g of N-S-di-Boc-D-cystein-N-hydroxysuccinimide ester, prepared by the method described in Liebig's Ann. Chem. 743, page 57 (1971) and 4.05 g of L-1,2,3,4-tetrahydroisoquinoline-3-carboxylic acid tert. butyl ester tosylate, prepared according to Example 1, are dissolved in 60 ml of dimethyl formamide. 1.28 ml of N-ethylmorpholine are added and the mixture is stirred over night at room temperature. Next, the solvent is distilled off in vacuo, the resinous residue is digested in water and dried in vacuo. Yield 4.49 g (18%) of a solid mass without sharp melting point.

(B)
D-Cysteinyl-L-1,2,3,4-tetrahydroisoquinoline-3-carboxylic acid 4.4 g of the compound prepared according to (A) are kept for 15 to 20 minutes at room temperature in 0.2N HCl in formic acid containing 5% of dithioglycol. The mixture is evaporated to dryness in vacuo and the residue is digested in ether. The solid product obtained is a little hygroscopic. Yield 1.44 g (56%). An elemental analysis, taking 3 to 5% water into consideration, was correct.

EXAMPLE 4

N-Acetyl-S-benzoyl-D-cysteinyl-L-1,2,3,4-tetrahydroisoquinoline-3-carboxylic acid 3.9 g of N-acetyl-S-benzoyl-D-cysteine-4-nitrophenyl ester, obtained by the method described in J. Org. Chem. 27, page 3329 (1962), are reacted according to Example 3(A) with 4.1 g of L-1,2,3,4-tetrahydroisoquinoline-3-carboxylic acid tert. butyl ester tosylate and 1.28 ml of N-ethylmorpholine. The crude product is purified by filtration of its chloroformic solution over silica gel. Yield 3.65 g (73%) of a semi-solid mass which is uniform in a thin layer chromatogram and the elemental analysis of which is satisfactory.

To split off the tert. butyl alcohol from the ester group, the compound is kept for 40 minutes in trifluoroacetic acid, which is then distilled off in vacuo. The residue is dissolved in aqueous 50% methanol and treated with a weakly basic ion exchanger in acetate form until the pH is shifted from about 2 to about 3 to 4. The exchanger is filtered off. After distillation of the solvent in vacuo and drying over P$_2$O$_5$, a hard pulverizable mass is obtained. Yield 2.5 g (81%). For analysis the cyclohexyl ammonium or dicyclohexyl ammonium salt is recrystallized from isopropanol. Elemental analysis of the salts is correct.

EXAMPLE 5

N-Acetyl-D-cysteinyl-L-1,2,3,4-tetrahydroisoquinoline-3-carboxylic acid 1 g of the compound obtained according to Example 4 is dissolved in 4N methanolic ammonia and kept for 2 hours under nitrogen. The reaction product is further treated as described in Example 2. Yield 0.54 g (71%).

EXAMPLE 6

N-(2-Methyl-3-acetylmercaptopropionyl)-L-1,2,3,4-tetrahydroisoquinoline-3-carboxylic acid (A) 2-Methyl-3-acetylmercaptopropionic acid-2,4,5-trichlorophenyl ester The trichlorophenyl ester is prepared in a known manner from 16.2 g of the acid, 19.7 g of 2,4,5-trichlorophenol and 22 g of dicyclohexyl carbodiimide in tetrahydrofurane. After filtration, the compound is purified by chromatography on silica gel using tetrahydrofuran as an eluant. Yield 29.8 g (79%), melting point 40°–41° C.

(B)
N-(2-Methyl-3-acetylmercaptopropionyl)-L-1,2,3,4-tetrahydroisoquinoline-3-carboxylic acid A salt is prepared from 1.77 g of 1,2,3,4-tetrahydroisoquinoline-3-carboxylic acid and 1.05 g of tetramethyl guanidine in 10 ml of methanol and under nitrogen. The methanol is distilled off in vacuo and the residue is dissolved under nitrogen in 10 ml of dimethyl formamide. 3.4 g of 2-methyl-3-acetylmercaptopropionic acid active ester prepared according to (A) and 0.1 g of 1-hydroxybenzotriazole in 10 ml of dimethyl formamide are added to the solution obtained and the whole is kept over night at room temperature. After distillation of the solvent, the product is purified as described in Example 1(E), whereupon 1.0 g of title compound is obtained, which is identical with the compound obtained according to Example 1(E).

EXAMPLE 7

N-(2-Methyl-3-nicotinoylmercaptopropionyl)-L-1,2,3,4-tetrahydroisoquinoline-3-carboxylic acid (A) Nicotinic acid N-hydroxysuccinimide ester The title compound is prepared in known a manner from 30.8 g of nicotinic acid, 34.5 g of N-hydroxysuccinimide and 55 g of dicyclohexyl carbodiimide in 800 ml of dimethyl formamide. When the reaction is terminated, the mixture is concentrated in vacuo to one third of its volume, cooled to 0° C., filtered and the filtrate is evaporated to dryness in vacuo. The residue is recrystallized from 200 ml of isopropanol. Yield 49.0 g, melting point 137° to 138° C.

(B)
N-(2-Methyl-3-nicotinoylmercaptopropionyl)-L-1,2,3,4-tetrahydrosioquinoline-3-carboxylic acid 3.3 g of active ester obtained according to (A) are reacted with 2.8 g of N-(2-methyl-3-mercaptopropionyl)-L-1,2,3,4-tetrahydroisoquinoline-3-carboxylic acid and 1.28 ml of N-ethylmorpholine in 50 ml of dimethyl formamide. The mixture is left to stand over night, the solvent is distilled off, the residue is digested in dilute acetic acid and water, dried in vacuo and taken up in a small amount of isopropanol. The cyclohexylammonium salt is prepared by adding cyclohexylamine and for purification the salt is recrystallized from isopropanol. The free compound is obtained by filtration of the solution of the salt in aqueous 50% methanol over a weakly acid ion exchanger. The solvent is distilled off in vacuo. After drying of the residue, a pulverizable resin is obtained. UV extinction curve and elemental analysis confirm the correct structure of the compound.

EXAMPLE 8

N-(2-Methyl-3-mercaptopropionyl)-L-1,2,3,4-tetrahydroisoquinoline-3-carboxylic acid 17.7 g of 1,2,3,4-tetrahydroisoquinoline-3-carboxylic acid are converted into the methyl ester hydrochloride using hydrochloric acid or thionyl chloride in methanol in known manner. After distillation of the solvent the compound is isolated by digestion with ether.

The dry residue is reacted as described in Example 1(D) with 16.2 g of 2-methyl-3-acetylmercaptopropionic acid, 12.8 ml of N-ethylmorpholine and 22 g of dicyclohexyl carbodiimide in methylene chloride. The reaction mixture is worked up as described in Example 1(D).

The oily residue is dissolved in 150 ml of dioxane/methanol 1:1. 2N NaOH is added drop by drop while stirring under nitrogen in order to maintain a pH of 12.5 to 13. When no more sodium hydroxide is consumed, the solution is treated with aqueous 50% methanol and the combined solutions are concentrated by evaporation in vacuo. The residue is digested with petroleum ether and dried in vacuo. Yield 7.8 g. According to thin layer chromatography the compound is identical with that of Example 2.

EXAMPLE 9

β,β-Dithiodiisobutyryl-bis-L-1,2,3,4-tetrahydroisoquinoline-3-carboxylic acid (A) 4 g of L-1,2,3,4-tetrahydroisoquinoline-3-carboxylic acid tert. butyl ester tosylate are reacted, in the presence of 1.28 ml of N-ethylmorpholine, with 1.2 g of β,β-dithiodiisobutyric acid, prepared as described in Svensk kem. Tidskr. 55, page 170 (1943), and 1.1 g of dicyclohexyl carbodiimide in 50 ml of dimethyl formamide. After filtration, the reaction product is precipitated with water and dried. For splitting the tert. butyl ester, the product is treated for 45 minutes with trifluoroacetic acid which is then distilled off in vacuo. The residue is dissolved in 80 ml of methanol. The solution is stirred in a small amount of weakly basic ion exchanger in acetate form and, after filtration, the reaction product is evaporated to dryness in vacuo. A resinous mass is obtained, which solidifies on prolonged standing under ether/petroleum ether and can then be triturated. It is preferably converted into its alkali metal or ammonium salt in which form it is easier to handle.

(B) 2 g of the compound prepared as described in A are dissolved in a mixture of ethanol and sodium phosphate buffer of pH 6. Iodine is added drop by drop and while stirring until the yellow coloration remains constant. The mixture is decolorized with thiosulfate and the ethanol is distilled off in vacuo. Next, the mixture is cautiously acidified with 4N hydrochloric acid to pH 1.5 to 2 and the title compound is shaken with ethyl acetate. The ethyl acetate solution is washed with a small amount of water, dried over $Na_2SO_4$ and concentrated in vacuo. Yield 1.77 g. For analysis the cyclohexyl amine salt is prepared in acetonitrile. Melting point 186° to 190° C. Elemental analysis correct.

EXAMPLE 10

3-Mercapto-2-methylpropionyl-1,2,3,4-tetrahydroquinoline-2-carboxylic acid 1.63 g of 2-methyl-3-acetylmercaptopropionic acid and 2.3 g of 1,2,3,4-tetrahydroquinoline-2-carboxylic acid methyl ester hydrochloride, prepared as described in Chem. Ber. 61, page 2377 (1928), are dissolved under nitrogen in 20 ml of dimethyl acetamide. 1.35 g of 1-hydroxy-benzotriazole, 1.28 ml of N-ethylmorpholine and 2.2 g of dicyclohexyl carbodiimide are successively added and the whole is stirred for 4 hours at room temperature. The reaction mixture is then filtered and the solvent is distilled off from the filtrate in vacuo. The residue is dissolved in 30 ml of methanol. The solution is stirred and 10 ml of 4N NaOH are added drop by drop and under nitrogen. 10 minutes after termination of the addition, 10 ml of 4N HCl are added, whereupon the mixture is evaporated to dryness in vacuo. After distillation of the solvent, the reaction product is purified by chromatography on 130 g of $SiO_2$ in a system of chloroform/isopropanol/acetic acid (50:10:3). Yield 2.3 g. Elemental analysis and NMR spectrum correct.

EXAMPLE 11

N-(2-Methyl-3-nicotinoylmercaptopropionyl)-1,2,3,4-tetrahydroquinoline-2-carboxylic acid 1.4 g of the compound obtained as described in Example 10 are dissolved in 10 ml of dimethyl formamide and reacted under nitrogen with 1.1 g of nicotinic acid N-hydroxysuccinimide ester, prepared in usual manner form nicotinic acid, N-hydroxy-succinimide and dicyclohexylcarbodiimide, melting point 137° to 138° C. The solvent is distilled off after 3 hours and the residue is chromatographed as described in Example 10. Yield 0.7 g. UV and NMR spectra confirm that the product is the desired compound.

EXAMPLE 12

N-(2-Methyl-3-acetylmercaptopropionyl)-indoline-2-carboxylic acid

The acid chloride is prepared from 2-methyl-3-acetylmercaptopropionic acid with a 10% excess of thionyl chloride in methylene chloride by heating for 3 hours. The acid chloride is obtained in pure form by distillation under 1 mm Hg.

1.9 g of the acid chloride are reacted under nitrogen with the tetramethylguanidinium salt of 1.63 g of indoline-2-carboxylic acid in dimethyl acetamide. After working up and purification as described in Example 10, 2.9 g of pure title compound are obtained with correct elemental analysis.

EXAMPLE 13

N-(2-Methyl-3-acetylmercaptopropionyl)-L-decahydroisoquinoline-3-carboxylic acid

A.
N-Benzyloxycarbonyl-L-decahydroisoquinoline-3-carboxylic acid 36 g of L-decahydroisoquinoline-3-carboxylic acid, prepared from the 1,2,3,4-tetrahydro compound by catalytic hydrogenation over 5% rhodium-on-charcoal at 60°–90° C. and 80–150 bars $H_2$ pressure in 90% strength acetic acid, are suspended in 200 ml of 1N NaOH. 30.2 ml of benzyloxycarbonyl chloride are added at 0°–5° C., while stirring vigorously, and 232 ml of 1N NaOH are added slowly at the same time and the mixture is stirred for a further 2 hours. It is then extracted twice with ether, disregarding a precipitate, and the aqueous solution is acidified with concentrated hydrochloric acid and is extracted by shaking with ethyl acetate. The ethyl acetate phase is washed with water and dried over $Na_2SO_4$. A resin is left as residue after removing the solvent by distillation in vacuo. This solid is dissolved in hot diisopropyl ether. After adding dicyclohexylamine, the salt is precipitated on cooling. Yield 49.1 g. The acid is liberated in the customary manner by means of potassium bisulfate/ethyl acetate.

B.
N-Benzyloxycarbonyl-L-decyhydroisoquinoline-3-carboxylic acid tert.-butyl ester 32 g of the compound obtained in (A) are dissolved in 250 ml of methylene chloride. 38.5 ml of tert.-butanol and 1 g of 4-dimethylaminopyridine are added and the solution of 22 g of dicyclohexylcarbodiimide in 60 ml of methylene chloride is added dropwise at 0° C., while stirring. The mixture is then stirred for 15 minutes at 0° C. and for 5 hours at room temperature, and is filtered and the filtrate is evaporated to dryness in vacuo. The residue is redissolved in methylene chloride and the solution is extracted by shaking successively with saturated sodium dicarbonate solution and potassium bisulfate/potassium sulfate solution, washed with water until it is neutral and dried over $Na_2SO_4$. Evaporation leaves an oily residue. Yield 32.0 g.

C. L-Decahydroisoquinoline-3-carboxylic acid tert.-butyl ester-toluenesulfonate 30.5 g of the compound obtained in (B) are dissolved in 300 ml of methanol and hydrogenated catalytically over palladium black, the pH value being kept at 5 by adding 1N toluenesulfonic acid in methanol by means of an autotitrator. When the reaction is complete, the catalyst is filtered off and the solvent is removed by distillation. The resinous residue solidifies on being triturated with ether and water. Yield 31.4 g. The compound is virtually pure according to chromatography and is distinguished from the starting material by a lower $R_f$ value in the thin layer chromatogram (silica gel).

D.
N-(2-Methyl-3-acetylmercaptopropionyl)-L-decahydroisoquinoline-3-carboxylic acid tert.-butyl ester 20.5 g of the tert.-butyl ester-tosylate obtained in (C) are dissolved in 200 ml of methylene chloride and 8.3 g of 2-methyl-3-acetylmercaptopropionic acid and 6.4 ml of N-ethylmorpholine are added, followed, while cooling with ice, by 11 g of dicyclohexylcarbodiimide, dissolved in 60 ml of methylene chloride. The mixture is stirred overnight at room temperature and filtered, the solvent is removed by distillation in vacuo and the residue is taken up in ethyl acetate. The solution is washed successively with $NaHCO_3$ solution, $KHSO_4/K_2SO_4$ solution and water, is dried over $Na_2SO_4$ and is evaporated in vacuo. This gives 15.9 g of an oil.

NMR ($CDCl_3$):1.20 (d, 3H); 1.40 (s, 9H); 2.13 (s, 3H); 1.1–5.1 (m, 18H).

E.
N-(2-Methyl-3-acetylmercaptopropionyl)-L-decahydroisoquinoline-3-carboxylic acid 13 g of the compound obtained in (D) are dissolved in 70 ml of trifluoroacetic acid, which is distilled off in vacuo after 45 minutes. The residue is partitioned between 180 ml of ethyl ether and 90 ml of saturated $NaHCO_3$ solution. The ether phase is discarded and the aqueous phase is acidified with concentrated hydrochloric acid and extracted three times with ethyl acetate. The combined ethyl acetate solutions are washed with water and dried over $Na_2SO_4$. The solvent is removed by distillation, the residue is taken up in ether and cyclohexylamine is added, while stirring, until the moist pH paper indicates a value of 8. After cooling the resulting suspension, the cyclohexylammonium salt ist filtered off and is washed with ether. After drying, it is recrystallised from isopropanol and acetonitrile. Yield 4.6 g. The free acid is obtained by suspending the salt between water and ethyl acetate/ether. The addition of $KHSO_4$ solution until pH 2 is reached produces complete solution. The phases are separated, the aqueous solution is washed with a little ethyl acetate and the combined organic phases are washed with a little water and dried over $Na_2SO_4$ and the solvent is removed by distillation in vacuo. The resinuous residue solidifies on being triturated with ether. Yield 3.0 g. Elementary analysis correct.

NMR ($DMSO-d_6$): 1.22 (d, 3H); 2.15 (s, 3H), 1.1–5.1 (m, 18H).

EXAMPLE 14

N-(2-Methyl-3-mercaptopropionyl)-L-decahydroisoquinoline-3-carboxylic acid 1.5 g of the compound prepared in Example 13(E) are kept in 8 ml of 5N ammonia in methanol for 2 hours under nitrogen. The solution is then evaporated to dryness in vacuo. The solid residue is dissolved in 10 ml of 50% strength aqueous methanol. The solution is filtered through a small column containing the strongly acid ion exchanger "Lewatit S 100" and the eluate is evaporated to dryness in vacuo. The resinuous residue is digested with petroleum ether, whereupon it solidifies. Drying in vacuo gives the title compound in a yield of 0.81 g. Elementary analysis correct.

NMR (CF$_3$COOH): 1.20 (d, 3H); 1.2–5.2 (m, 19H).

EXAMPLE 15

N-D-Cysteinyl-L-decahydroisoquinoline-3-carboxylic acid

A.
N-S-Di-Boc-D-cysteinyl-L-decahydroisoquinoline-3-carboxylic acid tert.-butyl ester 4.36 g of N-S-Di-Boc-D-cysteine-N-hydroxysuccinimide ester, prepared analogously to Liebig's Ann. Chem. 743 (1971), page 57 and 4.1 g of L-decahydroisoquinoline-3-carboxylic acid tert.-butyl ester-tosylate, prepared in accordance with Example 13, are dissolved in 60 ml of dimethylformamide. 1.28 ml of N-ethylmorpholine are added and the mixture is stirred overnight at room temperature. The solvent is then removed by distillation in vacuo and the resinous residue is digested with water and dried in vacuo. Yield 4.38 g of a solid mass having an unsharp melting point.

B. D-Cysteinyl-L-decahydroisoquinoline-3-carboxylic acid 4.4 g of the compound obtained in (A) are kept in 0.2N HCl in formic acid, containing 10% of ethyl mercaptan, for 15–20 minutes at room temperature. The mixture is evaporated to dryness in vacuo and the residue is digested with ether. The solid product obtained is somewhat hygroscopic. Yield 1.44 g (56%). After allowing for 3–5% of water, the elementary analysis is correct.

EXAMPLE 16

N-Acetyl-S-benzoyl-D-cysteinyl-L-decahydroisoquinoline-3-carboxylic acid 3.9 g of N-acetyl-S-benzoyl-D-cysteine 4-nitrophenyl ester, obtained analogously to J. Org. Chem. 27 (1962), page 3329, are reacted in accordance with Example 15(A) with 4.2 g of L-decahydroisoquinoline-3-carboxylic acid tert.-butyl ester-tosylate and 128 ml of N-ethylmorpholine. The crude product is purified by filtration in solution in chloroform over silica gel. Yield 3.52 g of a semi-solid mass which has a single-substance thin layer chromatogram and exhibits a satisfactory elementary analysis. The tert.butyl alcohol is split off from the ester group by keeping the compound for 40 minutes in trifluoroacetic acid, which is then removed by distillation in vacuo. The residue is dissolved in 50% strength aqueous methanol and is treated with a weakly basic ion exchanger in the acetate form until the pH value has fallen back from about 2 to about 3–4. The exchanger is then filtered off. Distilling off the solvent in vacuo and drying the residue over P$_2$O$_5$ gives a hard, powderable mass. Yield 2.1 g. For analysis, the cyclohexylammonium or diycylohexylammonium salt is recrystallized from isopropanol. The salts have a correct elementary analysis.

EXAMPLE 17

N-Acetyl-D-cysteinyl-L-decahydroisoquinoline-3-carboxylic acid 1 g of the compound obtained in Example 16 is dissolved in 4N methanolic ammonia and is kept under nitrogen for 2 hours. The mixture is worked up as in Example 14. Yield 0.50 g.

NMR (CF$_3$COOH): 2.1 (s, 3H); 1.1–5.2 (20H).

EXAMPLE 18

2-Methyl-3-acetylmercaptopropionyl-L-decahydroisoquinoline-3-carboxylic acid

A. 2-Methyl-3-acetylmercaptopropionic acid 2,4,5-trichlorophenylester

The trichlorophenyl ester is prepared in a known manner from 16.2 g of the acid, 19.7 g of 2,4,5-trichlorophenol and 22 g of dicyclohexylcarbodiimide in tetrahydrofuran. After filtration, the compound is purified by chromatography over silica gel using tetrahydrofuran as the migrating agent. Yield 29.8 g (79%). Melting point 40°–41°.

B.
2-Methyl-3-acetylmercaptopropioyl-L-decahydroisoquinoline-3-carboxylic acid

The corresponding salt is prepared from 1.8 g of decahydroisoquinoline-3-carboxylic acid and 1.05 g of tetramethylguanidine in 10 ml of methanol, under nitrogen, the methanol is removed by distillation in vacuo and the residue is dissolved in 10 ml of dimethylformamide under nitrogen. 3.4 g of the 2-methyl-3-acetylmercaptopropionic acid active ester obtained in (A) and 0.1 g of 1-hydroxybenzotriazole in 10 ml of dimethylformamide are added to this solution and the whole mixture is kept overnight at room temperature. After removing the solvent by distillation, the product is purified as described in Example 13(E) to give 0.95 g of the tilte compound, which is identical with the compound obtained in Example 13(E).

EXAMPLE 19

N-(2-Methyl-3-mercaptopropionyl)-L-decahydroisoquinoline-3-carboxylic acid 17.9 g of decahydroisoquinoline-3-carboxylic acid are converted into the methyl ester-hydrochloride in a known manner by means of hydrochloric acid or thionyl chloride in methanol. After distilling off the solvent, the compound is isolated by digesting the residue with ether.

The dry residue is reacted in accordance with Example 13(D) with 16.2 g of 2-methyl-3-acetylmercaptopropionic acid, 12.8 ml of N-ethylmorpholine and 22 g of dicyclohexylcarbodiimide in methylene chloride. The mixture is worked up analogously to Example 13(D).

The oily residue is dissolved in 150 ml of 1:1 dioxane-methanol. 2N NaOH is added dropwise, while stirring and under nitrogen, and the pH value is kept at 12.5–13. When no further sodium hydroxide solution is consumed, the solution is treated with a strongly acid ion exchanger in 50% strength aqueous methanol and the combined solutions are concentrated in vacuo. The residue is digested with petroleum ether and dried in vacuo. Yield 7.8 g. The compound is identical, in terms of thin layer chromatography, with the compound obtained in Example 14.

EXAMPLE 20

β,β-Dithiodiisobutyryl-bis-L-decahydroisoquinoline-3-carboxylic acid

A. 4.2 g of L-decahydroisoquinoline-3-carboxylic acid tert.-butyl ester-tosylate are reacted with 1.2 g of β,β-dithiodiisobutyric acid, prepared as in Svensk kem. Tidskr. 55 (1943), page 170, and 1.1 g of dicyclohexylcarbodiimide in 50 ml of dimethylformamide in the presence of 1.28 ml of N-ethylmorpholine. After filtering the mixture, the reaction product is precipitated with water and is dried. The tert.-butyl ester is split by treating the product for 45 minutes with trifluoroacetic acid, which is then removed by distillation in vacuo. The residue is dissolved in 80 ml of methanol and the solution is stirred with a little of a weakly basic ion exchanger in the acetate form and, after filtration, is evaporated to dryness in vacuo. A resinous mass is formed, which solidifies and can be triturated after standing for a fairly long period under ether/petroleum ether. It is advantageously converted into an alkali metal salt or ammonium salt and is then easier to handle.

B. 2 g of the compound prepared in example 14 are dissolved in a mixture of ethanol and a sodium phosphate buffer of pH 6. Iodine is added dropwise, while stirring, until a constant yellow coloration is obtained, the mixture is decolorized with thiosulfate and the ethanol is removed by distillation in vacuo. The mixture is then acidified cautiously to pH 1.5-2 with 4N hydrochloric acid and the title compound is extracted by shaking with ethyl acetate. The ethyl acetate solution is washed with a little water, dried over Na₂SO₄ and concentrated in vacuo. Yield 1.77 g. For analysis, the cyclohexylamine salt is prepared in acetonitrile. Elementary analysis correct.

EXAMPLE 21

3-Mercapto-2-methylpropanoyldecyhydroquinoline-2-carboxylic acid 1.63 g of 2-methyl-3-acetylmercaptopropionic acid and 2.4 g of decahydroquinoline-2-carboxylic acid methyl esterhydrochloride are dissolved in 20 ml of dimethylacetamide under nitrogen. 1.35 g of 1-hydroxybenzotriazole, 1.28 ml of N-ethylmorpholine and 2.2 g of dicyclohexylcarbodiimide are also added successively and the mixture is stirred for 4 hours at room temperature. It is then filtered and the solvent is removed from the filtrate by distillation in vacuo. The residue is dissolved in 30 ml of methanol. The solution is stirred and 10 ml of 4N NaOH are added dropwise, under nitrogen, and, 10 minutes after the addition has been completed, 10 ml of 4N HCl are added. The mixture is then evaporated to dryness in vacuo. After removing the solvent by distillation, the residue is purified by chromatography over 130 g of SiO₂ using the system 50:10:3 chloroform/isopropanol/acetic acid. Yield 2.2 g. Elementary analysis correct.

NMR (CF₃COOH): 1.21 (d, 3H); 1.2-3.8 (m, 12H); 4.96 (m, 1H).

EXAMPLE 22

2-Methyl-3-acetylmercaptopropionyloctahydroindole-2-carboxylic acid

The acid chloride is prepared from 2-methyl-3-acetylmercaptopropionic acid by warming for 3 hours with a 10% excess of thionyl chloride in methylene chloride, and the product is obtained in a pure state by distillation under a pressure of 1 mm Hg. 1.9 g of the acid chloride are reacted with the tetramethylguanidinium salt of 1.63 g of octahydroindoline-2-carboxylic acid in dimethylacetamide under nitrogen. Working up and purifying analogously to Examle 22 gives 2.9 g of the pure title compound having a correct elementary analysis.

EXAMPLE 23

2-Methyl-3-mercaptopropionyloctahydroindole-2-carboxylic acid

The acetyl group is split off analogously to Example 14 from the compound prepared in Example 22 and the product is worked up as described in Example 14. A resin, having a correct elementary analysis is obtained.

What is claimed is:

1. Compound of the formula I

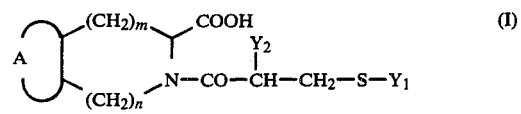

in which
n denotes 0 or 1, m denotes 1 or 2, but (n+m)≦2,
A together with the bridgehead carbon atoms denotes a benzene or a cyclohexane ring,
Y₁ denotes hydrogen, (C₁-C₆)-alkanoyl or (C₅-C₈)-cycloalkanoyl, benzoyl or a radical of the formula II,

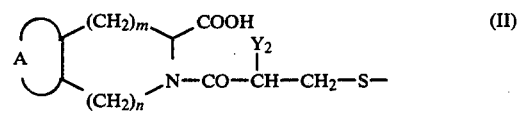

or, if
A is part of a benzene ring then Y₁ is as defined above or denotes nicotinoyl, and
Y₂ denotes amino, (C₁-C₆)-alkanoylamino, (C₅-C₈)-cycloalkanoylamino or benzoylamino,
or, if A is part of a benzene ring then Y₂ is as defined above or denotes nicotinoylamino.

2. The compound defined in claim 1 wherein n is 0 and m is 1.

3. The compound defined in claim 1 wherein n is 0 and m is 2.

4. The compound defined in claim 1 wherein m and n are 1.

5. The compound defined in claim 1 wherein m and n are 1 and Y₂ is amino, (C₁-C₆)-alkanoylamino, (C₅-C₈)-cycloalkanoylamino, benzoylamino or nicotinoylamino.

6. The compound defined in claim 1 wherein A is part of a benzene ring.

7. The compound defined in claim 1 wherein A is part of a cyclohexane ring.

8. A compound as in claim 1 which is N-acetyl-S-benzoyl-D-cysteinyl-L-1,2,3,4-tetrahydroisoquinoline-3-carboxylic acid.

9. A compound as in claim 1 which is N-D-cysteinyl-L-1,2,3,4-tetrahydroisoquinoline-3-carboxylic acid.

10. A compound as in claim 1 which is N-acetyl-D-cysteinyl-L-1,2,3,4-tetrahydroisoquinoline-3-carboxylic acid.

11. A compound as in claim 1 which is N-D-cysteinyl-L-decahydroisoquinoline-3-carboxylic acid.

12. A compound as in claim 1 which is N-acetyl-S-benzoyl-D-cysteinyl-L-decahydroisoquinoline-3-carboxylic acid.

13. A compound as in claim 1 which is N-acetyl-D-cysteinyl-L-decahydroisoquinoline-3-carboxylic acid.

14. A method for treating hypertension which comprises administering to a patient afflicted with hypertension a hypotensively effective amount of a compound as in claim 1.

15. A composition comprising a hypotensively effective amount of a compound as claimed in claim 1 and a pharmaceutically acceptable carrier compounds.

* * * * *